United States Patent [19]

Ferguson

[11] Patent Number: 4,975,106
[45] Date of Patent: Dec. 4, 1990

[54] ANAEROBIC DIGESTION OF FISH WASTES

[75] Inventor: James R. Ferguson, Cape Elizabeth, Me.

[73] Assignee: Biotherm International, Inc., South Portland, Me.

[21] Appl. No.: 809,482

[22] Filed: Dec. 16, 1985

[51] Int. Cl.$^5$ .............................................. C05F 11/08
[52] U.S. Cl. .......................................... 71/10; 71/16; 71/904
[58] Field of Search .......................... 71/1, 10, 904, 16

[56] References Cited

U.S. PATENT DOCUMENTS

| | | | |
|---|---|---|---|
| 2,029,702 | 2/1936 | Buswell et al. | 210/603 |
| 2,560,011 | 7/1950 | Trudel | 71/16 X |
| 3,220,945 | 11/1965 | Torpey | 210/609 |
| 3,245,776 | 4/1966 | Rubin | 71/1 |
| 3,259,566 | 7/1966 | Torpey | 210/603 |
| 3,333,939 | 8/1967 | Davis et al. | 71/29 |
| 3,468,794 | 9/1969 | Amero | 210/608 |
| 3,598,606 | 8/1971 | Spinelli | 530/420 |
| 3,980,462 | 9/1976 | Corte et al. | 71/1 |
| 4,022,665 | 5/1977 | Ghosh et al. | 435/167 |
| 4,043,788 | 8/1977 | Fryer | 71/29 |
| 4,126,439 | 11/1978 | Stekoll | 71/16 |
| 4,383,845 | 5/1983 | Rutherford | 71/16 |

OTHER PUBLICATIONS

Anaerobic Digestion of Red and Chum Salmon Wastes, 1982, NTIS, PC A04MF A10-Abstract.

Primary Examiner—Ferris H. Lander
Attorney, Agent, or Firm—Lahive & Cockfield

[57] ABSTRACT

A method and apparatus for anaerobic digestion of fish wastes and production of useful by-products including fertilizer and biogas. The method includes grinding up the fish wastes and adding liquid to create a suspension of up to 25% solids; optionally adding lipase to break down the fish oil; and anaerobically digesting the fish suspension over a period of approximately 20 days at a temperature in the range of 35°-55° C. with mixing provided by recirculation or other means. After digestion, the suspension is pumped to a secondary chamber for storage, further breakdown by mechanical means such as agitation or recirculation, centrifugation to remove suspended solids, production of an enhanced fertilizer by the addition of seaweed, urea, nitrogen, potash and chelated micronutrients, deodorization, by the addition of potassium permanganate, treatment to reduce the B.O.D. or evaporation to reduce liquid.

19 Claims, 1 Drawing Sheet

ANAEROBIC DIGESTION OF FISH WASTES

BACKGROUND OF THE INVENTION

This invention is generally in the field of waste treatment, and particularly in the area of recycling of fish wastes.

Disposal of fish wastes using conventional technology presents a number of problems Of primary importance is the odor associated with the long-term storage of the fish wastes Other problems include the cost of disposal and EPA regulations which prohibit dumping of fish wastes into the sewer or harbor water.

Historically, after extraction of useful oils, fish wastes have been rendered by a cooking process into a fish meal. Due to the odorous nature of this rendering process and to poor market conditions, many waste processing companies are having great difficulties in operating profitably and have been forced to close down.

Chemicals have also been used to aid in the disposal of fish wastes. For example, a strong base such as potassium hydroxide may be used to hydrolyze the fish wastes. U.S. Pat. No. 3,598,606 teaches a process for making a fish meal using sodium hexametaphosphate to insolubilize protein fractions. U.S. Pat. No. 4,043,788 to Fryer discloses a process for making a fertilizer by combining neutralized, hydrolyzed fish or fish waste with a solubilized seaweed and chelated plant nutrients. The fish is hydrolyzed by boiling in potassium hydroxide. U.S. Pat. No. 4,383,845 to Rutherford also discloses a foliar growth-promoting mixture including a liquid seaweed base, a fish emulsion consisting of fish solids which have been degraded under pressure with heat on the addition of an alkaline composition, liquid humus, and a mixture of carbohydrates, enzymes, and vitamins. The disadvantages of these processes are that they use strong chemical bases and heat or pressure to degrade the fish wastes, there is no method for eliminating the odor problem, and there is no process for handling high concentrations of fish oil such as that found in wastes from fish species such as menhaden or herring.

As shown by Torpey U.S. Pat. No. 3,259,566 and Ghosh et al., U.S. Pat. No. 4,022,665, anaerobic digestion has been used to convert organic wastes such as human sewage into a biogas consisting mainly of methane and carbon dioxide and other simple organic compounds. However, high oil contents from some fish species could cause mixing problems if conventional digestion apparatus were used.

It is therefore an object of the invention to provide a method and apparatus for disposal of fish and fish wastes in an economical, environmentally acceptable way, which is relatively odor-free.

It is a further object of the invention to provide a method and apparatus for producing commercially useful by-products of the disposal of fish wastes.

It is a still further object of the invention to provide a method and apparatus for economically manufacturing fertilizer containing protein, trace elements, and micronutrients It is another object of this invention to provide a method for disposal of fish wastes from fish species containing large amounts of fish oil without extensive chemical treatment.

It is a still further object of the invention to produce a stable digested fish wastes composition which does not contain viable pathogenic organisms or toxins.

SUMMARY OF THE INVENTION

The present invention is a process, and apparatus, for the disposal of fish and fish waste which is efficient, produces little odor, does not require extensive storage capacity, and yields commercially useful by-products including biogas and fertilizer.

The process consists of grinding up wastes from fish and other aquatic organisms, adding liquid to a level of up to 25% solids, adding lipase if the fish species contains a large quantity of fish oil, and storing the fish waste suspension for approximately 24 hours; pumping the fish suspension into a tank for anaerobic digestion for a period of approximately 10 to 20 days at a temperature in the range of 35 to 55° C. in the presence of a mixed culture of anaerobic bacteria with mixing to prevent the formation of a hard crust on the surface and the separation-of the fish oil; and pumping the digested mixture to a secondary chamber for storage and further breakdown by mechanical means such as agitation, recirculation, or compressed gas The material can then be further processed by centrifugation to remove suspended solids, addition of seaweed, urea, nitrogen, potash, potassium, and micronutrients to produce fertilizer, deodorization by the addition of potassium permanganate or other oxidant, treatment to reduce the B.O.D. or evaporation to produce a solid protein mixture.

The fish wastes are digested under anaerobic conditions using a mixed culture of mesophyllic or thermophyllic anaerobic organisms obtained from any of a number of different sources, including manure In the digestion tank mixing is provided, for example, by recirculation of the liquid which in some instances may include a second tank, or by bubbling a gas such as nitrogen through the fish mixture. The level of liquid in the digestion tank is preferably maintained by a liquid manifold or other liquid storage and valving means.

Useful by-products of the process include biogas, a mixture of carbon dioxide, methane and other gases, which can be separated by scrubbing, compressed for storage, incinerated, or utilized in a boiler or incinerator for generation of power, a protein solids mixture for use as an animal feed supplement, and fertilizer which is produced from the digested fish wastes. The fertilizer can be enhanced by the addition of seaweed in powder or liquid form, and other chemicals.

The invention will be more particularly described in connection with the accompanying drawing and tables

DETAILED DESCRIPTION OF THE INVENTION

Figure 1:
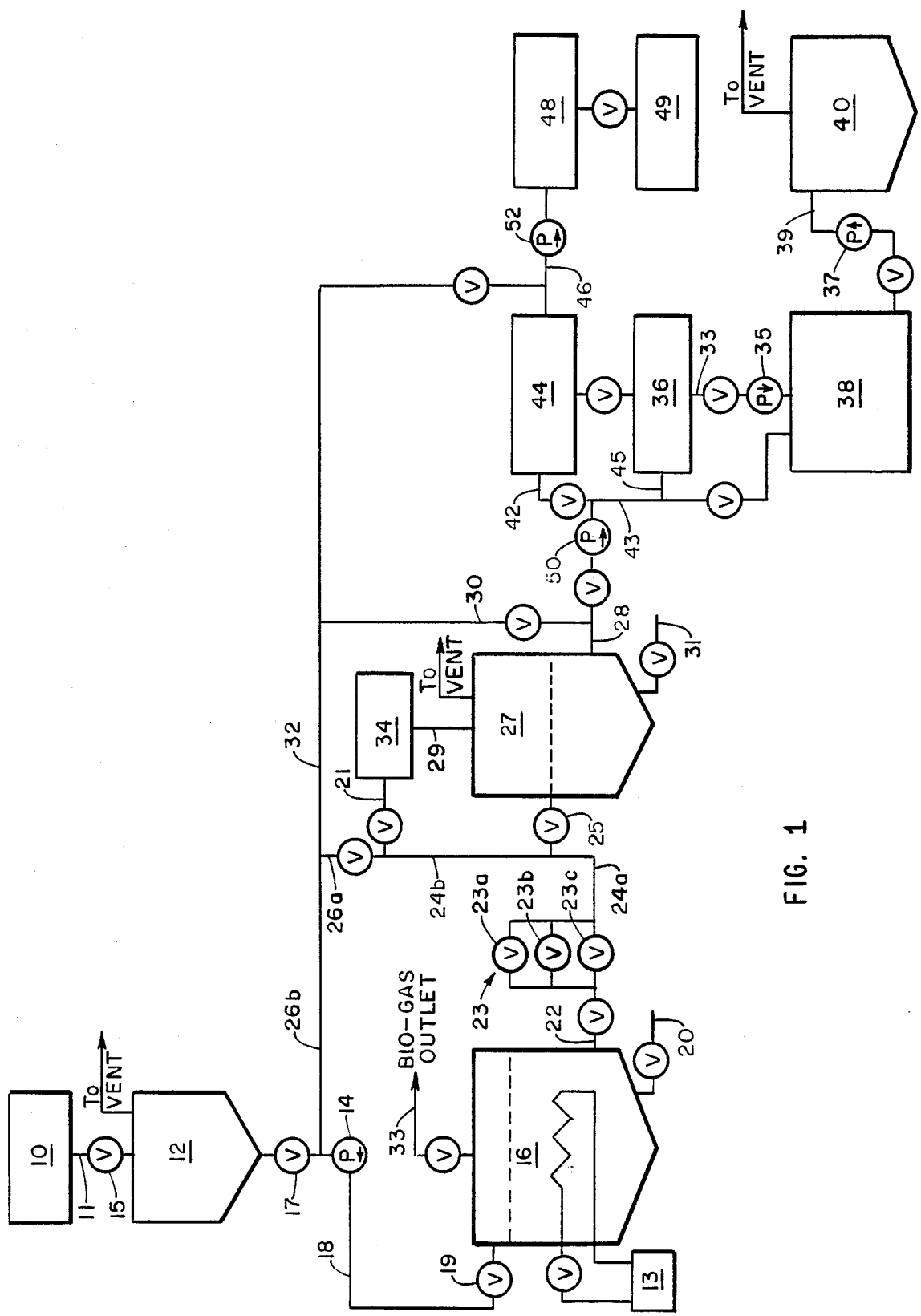
FIG. 1 is a schematic drawing of the method of the invention, as well as of optional variants thereof.

Referring to FIG. 1, whole fish, fish parts or racks containing bone, tissue, skin, blood, and wastes from other aquatic organisms such as crabs and shrimps, collectively referred to as "fish wastes", are first ground up in a fish grinder 10 to as small a size as is practical, for example using a 5 mm die. The advantages of the small particle size are the increased surface area available to the microorganisms and ease in pumping. Other known and equivalent methods for reducing particle size may also be used.

The ground-up fish waste is fed through a pipe 11 and valve 15 into a sealed storage tank 12 until sufficient wastes for further processing accumulate or until a previous digestion cycle is complete. Temperature controls on the tank 12 are optional, depending upon the source of the fish and the length of the storage period. The stored fish waste is then pumped via a valve 17, a diaphragm-pump 14 or other suitable pump, an inlet pipe 18 and a valve 19 to a primary anaerobic digestion tank 16.

It is important to maintain mixing of the digesting fish wastes in the digestion tank 16 in order to avoid buildup of a hard, crusty-like material on the surface of the fish wastes and to prevent separation of the fish oils. The mixing action also provides increased contact between the microorganisms and fresh substrate and reduces buildup of solids on the bottom of the tank 16. The fish wastes can be fed into the digestion tank 16 in either a batch manner or in a continuous manner. Mechanical agitation or recirculation may be used with either feeding method to provide adequate mixing. In one method of recirculation the digesting fish wastes are pumped through an outlet pipe 22 preferably at or near the bottom of the tank 16 through pipes 24a, 24b, 26a, 26b and 18 back into the tank 16. Preferably, the inlet pipe 18 from the storage tank 12 is connected to the digestion tank 16 above the level of the liquid therein so that the incoming mixture breaks up the surface of the digesting mixture. The constant inflow of liquid onto the top of the digesting material from the inlet pipe 18 breaks up the surface and helps to prevent formation of a crust.

Alternatively or in combination with such recirculation, gas may be bubbled up from an inlet pipe 20 at the bottom of the digestion tank 16 through the fish waste mixture. Any gas other than oxygen may be used, although an inert gas or a gas such as methane or nitrogen is preferred. By introducing the gas at the bottom of the tank 16, sediments as well as the crust on the top of the mixture are dispersed.

Another method of recirculation which is effective to provide the desired mixing action in the tank 16 is described below in connection with a storage tank 27.

Large amounts of fish oil from high-lipid species of fish such as herring and menhaden present mixing problems in the digestion tank 16 and require a longer digestion time than do protein and carbohydrate wastes. To ensure complete, rapid digestion of the lipid material, the ground-up fish in the storage tank 12 can be pretreated for a period of approximately 24 hours with a lipase or other enzyme which breaks down fats. The enzyme is added directly to the storage tank 12. More than one enzyme may be utilized to provide increased enzymatic breakdown over wider pH and temperature ranges. Other chemicals may also be added to adjust pH or other conditions to enhance enzymatic activity. It is preferable to mix the material in the storage vessel 12 continuously when using lipase to digest the fish wastes, and such mixing can be accomplished by any known means (not illustrated).

The digestion tank 16 contains a culture of anaerobic microorganisms. A preferred source of organisms is a culture of anaerobically digested cattle manure which has been fed a gradually increasing amount of organic compounds over a period of approximately 60 days in the digestion tank 16. Other sources of anaerobic organisms include sewage, sludge, manure from other animals, or mud from the bottom of a pond. The types of organisms which are used determine the time and temperature of digestion. For example, when mesophyllic organisms are used, fish wastes in the digestion tank 16 are typically substantially completely digested within a period of approximately 20 days at a preferred temperature in the range of 90–100° F. (35° C.). Thermophyllic organisms may be utilized to digest the fish wastes at an approximate temperature of 55° C. When thermophyllic organisms are utilized, substantially complete digestion takes approximately half as long The disadvantage of using the higher temperature organisms is the increased energy requirement. Heating of the digestion tank 16, if required, is provided by an immersion heater 13 circulating water at approximately 200° F. to heat the digestion tank contents Alternatively, a hot water jacket or heat exchanger around the pipe 18 (not shown) may be used to provide heating In actual operation, however, the system is flexible enough for digestion to occur at temperatures as low as 60° F. (25° C.).

When the digestion tank 16 is initially set up, the tank is cleared of air and purged with nitrogen, and then the culture is fed into the tank. Fish waste is then fed into the tank according to whether a batch or a continuous process is employed For a batch process the fish waste is fed into the tank at a rapid rate until a predetermined level below the connection of the pipe 18 is reached. Then the inflow is stopped and the contents of the tank are retained for digestion until approximately 95% of the connective tissue is digested, for example 20 days. For a continuous process the rate of inflow of fish waste is gradual and is increased to a steady rate bearing a predetermined relationship to the volume of material below the predetermined level in the tank. This relationship is such that it would require the same time period, for example 20 days, to fill the initially empty tank up to the predetermined level. At a given rate of inflow, a higher level corresponds to a longer time period for digestion, and vice versa.

A manifold 23 is used in conjunction with a secondary tank 27 to maintain a variable liquid level in the tank 16. Liquid flows through the pipe 22 into the manifold 23 where a selected valve 23a or 23b and a valve 25 are opened to vary the hydraulic retention time and total volume of liquid in the digestion tank 16. For this purpose a valve 23c is closed The liquid levels shown in the drawing correspond to the valve 23a being open and the valves 23b and 23c being closed.

As raw material is added to the digestion tank 16, digested fish wastes are removed from the tank through the pipes 22 and 24a and the valve 25 into the secondary storage tank 27 where additional digestion may occur. The digested material may be further blended in this tank by using mechanical means, such as an impellor or by the introduction of compressed gas through a pipe 31 at or near the bottom of the tank 26. This mechanical agitation aids further breakdown of any undigested fish wastes present in the secondary tank 27. The microorganisms entering the storage tank 27 gradually die as the remaining material is digested.

A further optional method of promoting blending of the liquid is to provide a recirculation loop including both of the tanks 16 and 27. The loop includes the pump 14, the pipe 18, the tank 16, pipes 22 and 24a, valve 25, tank 27, outlet pipe 28 and pipes 30, 32 and 26b. This recirculation may be employed to maintain the liquid level in the tank 16, to return liquid to it for further digestion, to control the percent solids in the tank 16, and to increase the overall system retention time.

The stored material can be fed from the secondary storage tank 27 through the pipe 28 and a pump 50 into any of a number of different tanks. For example, the stored, digested fish waste may be pumped through pipes 43 and 45 into a tank 36 where additional materials such as seaweed can be blended into the digested mixture using conventional blending apparatus, thus forming an enhanced fertilizer composition.

Fertilizer blends are designed to give optimum plant response in each specialized application Fertilizers rich in nitrogen (N) result in dark green foliage and active vegetative growth. Phosphorous (P), in addition to promoting seed germination, healthy seedlings, general plant vigor and hastened plant maturity, is necessary in plants that produce flowers, seeds and grain. Potassium (K), usually in the form of potash, is important in the formation and transportation of starch, sugar and other carbohydrates within the plant and also fosters root development. Applications to seed and soil are intended to promote early seedling growth with emphasis on promoting vital early root development. Foliar products are designed to promote vegetative development or to support heavier seed set. Thus, the basic fertilizer components are blended for specific N-P-K ratios depending upon the desired plant response.

However, plants need other elements such as sulphur, calcium, iron, magnesium, manganese, zinc and the like for balanced nutrition. In general, these are taken from the soil, depleting the soil unless being added in the fertilizer. Testing has shown that the fertilizer base produced from the digestion of salt water fish according to this invention contains most of these micronutrients so that minimal augmentation of the fertilizer in the blending stage is necessary. The following are examples of useful fertilizer compositions made by the addition of N, P, K, micronutrients and seaweed to the digested fish wastes produced by the above described process

TABLE 1

| Fertilizers | | |
|---|---|---|
| Application Method | Crop | N-P-K Ratio |
| Seed | Grass Family | 4-12-8 & Micronutrients |
| Treatment | Broadleaf Family | 3-12-10 & Micronutrients |
| Soil | Crop Starter | 4-16-16 & Micronutrients |
| Foliar | Fibers | 12-12-3 & Micronutrients |
| | Seed Crops | 12-8-4 & Micronutrients |
| | Lawn & Garden | 12-4-8 & Micronutrients |
| | House Plants | 2-6-6 & Micronutrients |
| Any Method | General Purposes | 8-8-8 & Micronutrients |

The application purpose generally determines the N-P-K ratio. The principal difference between the two products designed for seed treatment relates to the P-K ratios for the grass (monocotyledonous) family as compared to the broadleaf (dicotyledonous) family. The grass family seeds are more sensitive to zinc availability, whereas the broadleaf seeds are more responsive to iron and magnesium with a lesser affinity for zinc. Soil preparation fertilizer is designed to stimulate crop development and therefore requires higher levels of phosphorous and potassium. The foliar blend for lawn and garden use is designed to enhance greening.

The product produced from fish wastes by this invention is unlike conventional hydrolyzed fish meal fertilizers since there is no chemical digestion of the protein, carbohydrate, or fats present in the fish waste. Also, it has unexpected antibacterial, antifungal and insect repellant properties. These properties are presently thought to be due to a product formed during the anaerobic digestion of the fish wastes which is not normally present in chemically digested material, such as an eight or ten carbon chain fatty acid, ester by-product or proteolytic enzyme.

The analysis of one sample of digested fish wastes at the outlet pipe 28 is shown in Table 2

TABLE 2

| Analysis of Digested Fish Wastes | |
|---|---|
| pH 7.2 | 7,900 mg Kjeldahl N/kg |
| 2.9% solids | 410 mg P/kg |
| 99.4% volatile solids | 1,400 mg K/kg |
| 0.6% ash | 2.2 mg Co/kg |
| 4.9% protein | 36 mg Fe/kg |
| 0.19% fat | 1.1 mg Mn/kg |
| 17,500 mg/kg suspended solids | 64 mg Mg/kg |
| B.O.D. 57,000 mg/kg | 5.4 mg Zn/kg |
| C.O.D. 59,000 mg/kg | |

The incoming raw fish producing the sample of Table 2 had a pH of 6.7 and consisted of 10% solids, 98.9% volatile solids, 1.1% ash, 6.8% protein and 5.5% fat.

The enhanced fertilizer or plant food supplement is made by adding to the digested fish wastes combinations of nitrogen, phosphorus and potash to provide primary plant nutrients, an oxidizer such as potassium permanganate to reduce substantially the odors from the digested fish wastes, chelated micronutrients and seaweed. Seaweed provides micronutrients, trace elements, growth hormones, cytokinin and other beneficial factors. The seaweed is added in either powder, granular or liquid form from a seaweed storage tank 34 to a concentration of approximately 4 to 5 weight percent. Addition may be to the tank 16 via pipe 21, pipes 26a and 26b, pump 14 and pipe 18, or to the secondary storage tank 27 via a pipe 29. Adding seaweed to the digestion tank 16 results in increased generation of biogas which is drawn out at an outlet 33 for collection in pressurized vessels, burned as fuel or incinerated. Micronutrients such as iron, copper, magnesium, boron, and manganese, which are essential for plant growth, are added at any convenient location to a concentration of approximately 4 to 5 weight percent or as required for specific plant or soil characteristics. In the usual formulations, the N-P-K ratio is the percent nitrogen (from the digested fish and urea), the percent phosphorus (from monoammonium phosphate and phosphoric acid), and the percent potassium (from muriate of potash and potassium chloride) based on the combined weight of the fish wastes and sources of other nitrogen, phosphorus and potassium. Surfactant (about 0.1%) is added to increase wetting of the liquid fertilizer. About 0.1% formaldehyde or other preservative may also be added.

The digested fish waste produced according to this invention and fertilizer products containing it as described above do not contain viable pathogenic organisms, and appear to have antibacterial properties. For example, when a sample of the fish waste fertilizer product was inoculated with a pathogenic organism, *Salmonella typhimurium*, incubated at ambient room temperature for about 24 hours, inoculated into a lactose enrichment broth and incubated for 24 hours at 35° C., inoculated into a selenite cysteine broth and incubated for 24 hours at 35° C., and then spread-plated onto MacConkey, XLD, and Hectoen Enteric agar plates and incubated for 24 and 48 hours at 35° C., no viable *Salmonella* organisms could be recovered. The fertilizer product also appears to be free of other pathogenic organisms, including fecal coliform and *Clostridia botulinum*, when the material is directly cultured. The same results were found when the digested fish wastes were assayed for the presence of fecal coliform, *Salmonella*, and *Clostridia botulinum*.

TABLE 3

Assay of Digested Fish Wastes and Fertilizer for Pathogenic Organisms 24 Hours after Inoculation with a Pure Culture.

| Organism | Anaerobically Digested Fish Wastes | Fertilizer 85-1 |
|---|---|---|
| Fecal Coliform₁ | N.D.* | N.D. |
| Salmonella₂ | N.D. | N.D. |
| Clostridia botulinum | N.D. | N.D. |
| Clostridia botulinum Type E 3 | | |
| vegetative cells | $1 \times 10^3 (0.05\%)$ | — |
| Spores | $3.4 \times 10^4 (0.08\%)$ | — |

*Not detectable at measured concentrations: 1:4, 1:8, 1:16, 1:32, 1:64, 1:128, 1:256, 1:512, 1:1024
1. Procedure from Official Methods of Official Analytical Chemists, 14th edition (AOAC Arlington, VA 1984)
2. Direct Culture procedure Manual of Clinical Microbiology, 4th edition (A.S.M. Washington, D.C., 1985)
3. Bacteriological Analytical Manual (FDA, Washington, D.C., 1985); N. Grecz et al, Appl. Environ. Micro, 43,331–337 (1982); J.C. Silas et al, Appl. Environ. Micro, 50,2220-1112 (1985)

The digested fish wastes were also tested for the presence of botulinum toxin. Botulism is a neuroparalytic disease frequently lethal to man and animals. Food-borne botulism is caused by ingestion of the toxin produced by the anaerobic spore-forming bacillus, *Clostridium botulinum*. Botulinal toxins are intracellular proteins produced as protoxins, liberated when the vegetative cell lyses, and activated to the maximum toxic state by proteolytic enzymes such as trypsin. There are seven recognized serotypes of botulinal toxins, types A through G. Type E is the type most prevalent in fresh water and marine sediments in North America. Fish is an excellent substrate for the production of type E toxin.

Trials were conducted on the fish digest and the formulated fertilizer product to determine if the toxin was present in the fish digest, what effect the digest would have on the viability of the vegetative cells and spores of *C. botulinum*, what effect the digest and constituents that comprise the fertilizer product would have on purified botulinum toxin E, and if toxin production occurred in an artificially *C. botulinum* inoculated sample of digest effluent Results are summarized below:

1. A fish wastes digest was negative for butulinum toxin, as tested using the following procedure: Two mls. of the fish digest were diluted with 6 mls. sterile 0.05 M phosphate buffer pH 6.0 containing 1 ml. Streptomycin (Amresco) and $10^6$ units of penicillin (Sigma Chemical Co.), activated by adding trypsin (Difco) and incubating at 37° C. for 30 minutes, and i.p. injected into mice. The mice were still healthy after 72 hrs., indicating the absence of any botulinum toxins. The fertilizer mixture could not be tested for the presence of toxin since it is itself toxic to the mice.

2. The fish wastes digest did not support the growth of *Clostridium botulinum* type E (Strain D8).

3. Degradation or survival of artificially introduced toxin type E into the finished fertilizer product could not be determined because of a chemical toxicity of the fertilizer to the test mice.

4. No botulinum toxin was produced after inoculation of *C. botulinum* spores into the fish wastes digest after a 10 day incubation period.

The digested fish wastes and fertilizer were also tested for growth of *Xanthomonas* species. Samples: digest with potassium permanganate and seaweed; digest with potassium permanganate, formaldehyde, and seaweed; fertilizer with potassium permanganate, betadyne, formaldehyde and surfactant; and fertilizer with potassium permanganate, betadyne, formaldehyde, phosphoric acid and surfactant were serially diluted to 1:1024 and inoculated with *Xanthomonas*. After 24 hours there was no growth in the first sample at serial dilutions of 1:4 to 1:256. In the second sample, there was no growth at dilutions up to 1:64. There was growth in the third sample. In the fourth tube there was no growth at dilutions up to 1:1024. Any growth which was detected may have been derived from the digestive culture rather than from the innoculation with *Xanthomonas*.

If the fertilizer product is to be applied in liquid form, the blended composition in the tank 36 may be pumped via a pipe 33 and pump 35 to a vessel 38 for further processing using high-speed emulsifying or homogenizing equipment. Any solids from the raw materials, particles from the blending operation, or other materials which are in suspension are thereby reduced in size to the point where they are less likely to settle during storage and can be filtered so they can be applied through spray nozzles without blockage. The homogenized, blended fertilizer is then pumped via a pump 37 through a pipe 39 to a tank 40 for storage prior to final packaging and shipment.

If a solid digested fish waste product is desired, the liquid portion of the stored digested material in the tank 27 is removed from this tank via pipe 28, pump 50 and a pipe 42 into an apparatus 44 for separation of the liquid and solids. Examples of useful apparatus include centrifuges and filter presses. Other conventional methods for separation of liquid from suspended solids may be used. The separated solids may be utilized directly as a soil conditioner or animal feed supplement. The liquid effluent is passed through a pipe 46 and pump 52 into an apparatus 48 for lowering the "biological oxygen demand" (B.O.D.) by removal of the organic compounds and other particles. A number of conventional methods such as ultrafiltration or reverse osmosis may be used to reduce the B.O.D. and to recover much of the single-cell protein and other solids in the liquid effluent. The recovered protein may be used in a manner similar to that for the solids removed by the apparatus 44. The treated liquid effluent may then be directly discharged into the sewer or harbor water or further treated in a tank 49 using a packed aerobic digestion process or other biological filter method.

In order to operate in a relatively odor free manner, it is preferred that all storage vessels be sealed and vented to a central area where the contaminated air is either scrubbed or incinerated. Incineration may be either by direct combustion or by using the contaminated air as combustion air for an electrical generator. As noted above, energy is provided for the combustion process by the biogas by-product removed from the digestion tank 16, and similar use may be made of the vented gas from the secondary storage tank 27. Biogas, consisting of approximately 50–70% methane with the remainder generally as carbon dioxide, may also be stored or piped for use elsewhere.

Although this invention has been described with reference to specific embodiments, it is understood that modifications and variations of the composition and methods of processing will occur to those skilled in the art. It is intended that all such modifications and variations be included within the scope of the appended claims.

What is claimed is:

1. A method for digestion of fish wastes comprising the steps of
preparing a culture of anaerobic microorganisms from material selected from the group comprising anaerobically digested cattle manure, manure from other animals, sewage, sludge and mud from the bottom of a pond, said preparation including the feeding of a gradually increasing amount of organic compounds to said material,
feeding the culture into a digestion tank,
grinding the fish wastes into small pieces and adding water thereto to make a suspension of up to 25% solids,
feeding said suspension into the tank at a gradual rate of inflow, increasing said rate to a steady rate and withdrawing material from the tank to maintain a predetermined level of contents therein, the tank being cleared of air and maintained at a temperature between about 15.5 and 55° C., while mixing the suspension in the tank sufficiently to prevent the buildup of a crust on the surface, said steady rate of inflow being such that it would require a predetermined digestion time to fill the tank, if initially empty, to said predetermined level, said digestion time being that required to cause approximately 95% of the connective tissue in the fish wastes to be anaerobically digested.

2. The method for digestion of fish wastes of claim 1 further comprising adding an enzymatic composition to the fish waste suspension before feeding into the tank to degrade the fish oil.

3. The method for digestion of fish wastes of claim 2 further comprising adding at least one lipase to the fish waste suspension and mixing for a period of approximately 24 hours before feeding into the tank.

4. The method of digestion of fish wastes of claim 1 further comprising adding mesophyllic anaerobic microorganisms during preparation of the culture, wherein the fish wastes are digested by the mesophyllic anaerobic microorganisms at an approximate temperature of 35°C.

5. The method for digestion of fish wastes of claim 1 further comprising adding culture, wherein the fish wastes are digested by the thermophyllic anaerobic microoranisms at an approximate temperature of 55° C.

6. The method for digestion of fish wastes of claim 1 further comprising mixing the components in the fish wastes suspension in the tank having different specific gravities.

7. The method for digestion of fish wastes of claim 6 wherein the mixing is by recirculating fish wastes suspension withdrawn from the bottom of the digestion tank and reintroduced into the digestion tank above the liquid level of the fish wastes suspension.

8. The method of digestion of fish wastes of claim 6 wherein the mixing is by introducing a non-oxygenating gas into the bottom of the digestion tank containing the fish wastes-microorganisms suspension.

9. The method of fish wastes digestion of claim 1 further comprising pumping the digested fish wastes-microorganisms suspension into a second storage tank.

10. The method of digestion of fish wastes of claim 9 further comprising mechanically breaking down the digested fish wastes.

11. The method of digestion of fish wastes of claim 9 further comprising adding compounds selected from the group consisting of nitrogen sources, potassium sources, phosphate sources, oxidants, potassium permanganate, seaweed, micronutrients, surfactants, urea, formaldehyde, pH adjusting agents and combinations thereof.

12. The method for digestion of fish wastes of claim 10 further comprising homogenizing the digested fish wastes suspension.

13. The method for digestion of fish wastes of claim 9 further comprising separating the liquid from the suspended solids.

14. The method of digestion of fish wastes of claim 13 further comprising decreasing the B.O.D. of the separated liquid.

15. The method of digestion of fish wastes of claim 14 wherein the B.O.D. is decreased using ultrafiltration.

16. The method of digestion of fish wastes of claim 14 wherein the B.O.D. is decreased using reverse osmosis.

17. The method for digestion of fish wastes of claim 1 further comprising treating the gas evolved during the digestion of the fish wastes by the microorganisms to remove odor-causing chemical compounds.

18. The method for disposal of fish wastes of claim 1 further comprising collecting biogas evolved during digestion of the fish wastes by the anaerobic microorganisms.

19. The method for disposal of fish wastes of claim 18 further comprising generating energy from the collected biogas.

* * * * *

UNITED STATES PATENT AND TRADEMARK OFFICE
CERTIFICATE OF CORRECTION

PATENT NO. : 4,975,106
DATED : December 4, 1990
INVENTOR(S) : James R. Ferguson

It is certified that error appears in the above-identified patent and that said Letters Patent is hereby corrected as shown below:

Column 3, line 50, cancel "hreakdown" and substitute --breakdown--

Column 8, line 62, cancel "carhon" and substitute --carbon--

Column 9, line 46, (claim 5), after "adding" insert --thermophyllic anaerobic microorganisms during preparation of the--

Column 10, line 43, (claim 18), cancel "disposal" and substitute --digestion--

Column 10, line 47, (claim 19), cancel "disposal" and substitute --digestion--

Signed and Sealed this

Eighth Day of September, 1992

Attest:

DOUGLAS B. COMER

Attesting Officer

Acting Commissioner of Patents and Trademarks